(12) United States Patent
Seder et al.

(10) Patent No.: US 9,688,287 B2
(45) Date of Patent: Jun. 27, 2017

(54) SITUATION AWARENESS SYSTEM AND METHOD

(71) Applicant: GM GLOBAL TECHNOLOGY OPERATIONS LLC, Detroit, MI (US)

(72) Inventors: Thomas A. Seder, Northville, MI (US); Roy J. Mathieu, Rochester Hills, MI (US); Joseph F. Szczerba, Grand Blanc, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 64 days.

(21) Appl. No.: 14/918,073

(22) Filed: Oct. 20, 2015

(65) Prior Publication Data

US 2016/0082979 A1    Mar. 24, 2016

Related U.S. Application Data

(63) Continuation of application No. PCT/US2014/035385, filed on Apr. 25, 2014.
(Continued)

(51) Int. Cl.
*G08G 1/01* (2006.01)
*B60W 50/14* (2012.01)
(Continued)

(52) U.S. Cl.
CPC ............. *B60W 50/14* (2013.01); *A61B 3/113* (2013.01); *A61B 5/0205* (2013.01);
(Continued)

(58) Field of Classification Search
CPC combination set(s) only.
See application file for complete search history.

(56) References Cited

U.S. PATENT DOCUMENTS

| 6,580,973 B2* | 6/2003 | Leivian | B60R 16/0231 |
| | | | 701/1 |
| 8,384,534 B2* | 2/2013 | James | B60Q 9/008 |
| | | | 340/435 |

(Continued)

FOREIGN PATENT DOCUMENTS

| CN | 201525262 U | 7/2010 |
| CN | 202357886 U | 8/2012 |

(Continued)

*Primary Examiner* — Travis Hunnings
(74) *Attorney, Agent, or Firm* — Quinn IP Law

(57) ABSTRACT

A situation awareness method can be used to provide information to a vehicle operator via first, second, and third substantially transparent ambient displays that are coupled to a windshield of a vehicle. The situation awareness method includes the following steps: (a) monitoring a physiological state of the vehicle operator; (b) monitoring a vehicle operating parameter of the vehicle; (c) monitoring a vehicle context data; (d) identifying a predetermined physiological condition based on the monitored physiological state of the vehicle operator; (e) identifying a predetermined vehicle operating condition based on the monitored vehicle operating parameter; (f) identifying a predetermined vehicle context condition based on the monitored vehicle context data; (g) adjusting a luminance of the first, second, and third substantially transparent ambient displays based on the identified predetermined physiological condition, the identified predetermined vehicle operating condition; and the identified predetermined vehicle context condition, respectively.

16 Claims, 2 Drawing Sheets

Related U.S. Application Data

(60) Provisional application No. 61/816,089, filed on Apr. 25, 2013.

(51) Int. Cl.

| | | |
|---|---|---|
| *B60K 35/00* | (2006.01) | |
| *B60K 28/06* | (2006.01) | |
| *B60Q 9/00* | (2006.01) | |
| *G06K 9/00* | (2006.01) | |
| *G05D 3/00* | (2006.01) | |
| *G08C 17/02* | (2006.01) | |
| *A61B 3/113* | (2006.01) | |
| *A61B 5/0205* | (2006.01) | |
| *A61B 5/00* | (2006.01) | |
| *G07C 5/02* | (2006.01) | |
| *G07C 5/08* | (2006.01) | |
| *F21V 8/00* | (2006.01) | |
| *G02B 27/01* | (2006.01) | |
| *G02B 27/09* | (2006.01) | |
| *A61B 5/024* | (2006.01) | |
| *A61B 5/053* | (2006.01) | |

(52) U.S. Cl.
CPC .......... *A61B 5/6893* (2013.01); *B60K 28/066* (2013.01); *B60K 35/00* (2013.01); *B60Q 9/00* (2013.01); *G02B 6/005* (2013.01); *G02B 27/0101* (2013.01); *G02B 27/0927* (2013.01); *G02B 27/0961* (2013.01); *G05D 3/00* (2013.01); *G06K 9/00845* (2013.01); *G07C 5/02* (2013.01); *G07C 5/08* (2013.01); *G08C 17/02* (2013.01); *A61B 5/02405* (2013.01); *A61B 5/0533* (2013.01); *B60K 2350/2013* (2013.01); *B60K 2350/2021* (2013.01); *B60K 2350/2052* (2013.01); *B60K 2350/352* (2013.01); *B60R 2300/8006* (2013.01); *B60R 2300/8093* (2013.01); *B60W 2050/146* (2013.01); *B60Y 2302/03* (2013.01); *G02B 2027/0112* (2013.01); *G02B 2027/0118* (2013.01); *G02B 2027/0141* (2013.01); *G02B 2027/0194* (2013.01)

(56) References Cited

U.S. PATENT DOCUMENTS

| | | | |
|---|---|---|---|
| 2002/0091473 A1* | 7/2002 | Gardner | G07C 5/0808 701/32.7 |
| 2004/0002638 A1 | 1/2004 | Yanagidaira et al. | |
| 2005/0084659 A1 | 4/2005 | Dunkel | |
| 2009/0161029 A1* | 6/2009 | Sakaguchi | H04N 9/3126 348/751 |
| 2010/0253489 A1 | 10/2010 | Cui et al. | |
| 2012/0259546 A1* | 10/2012 | Kim | G02B 27/01 701/527 |
| 2015/0243168 A1* | 8/2015 | Roelle | G08G 1/133 340/995.27 |
| 2016/0009295 A1* | 1/2016 | Chun | A61B 5/6893 701/32.9 |
| 2016/0023666 A1* | 1/2016 | Lee | B60W 50/14 701/33.4 |
| 2016/0109701 A1* | 4/2016 | Goldman-Shenhar | G02B 27/01 345/8 |

FOREIGN PATENT DOCUMENTS

| | | |
|---|---|---|
| CN | 202806308 U | 3/2013 |
| DE | 4211728 A1 | 10/1993 |
| DE | 102004005816 A1 | 9/2005 |
| DE | 102005059216 A1 | 1/2007 |
| IE | 102009010623 A1 | 9/2010 |
| JP | 2007062516 A | 3/2007 |

\* cited by examiner

SITUATION AWARENESS SYSTEM AND METHOD

CROSS-REFERENCE TO RELATED APPLICATIONS

This application is a continuation of, and claims priority to, International Patent Application No. PCT/US2014/035385, filed on Apr. 25, 2014, which in turn claims priority to and the benefit of U.S. Provisional Application No. 61/816,089, filed Apr. 25, 2013, each of which is hereby incorporated by reference in its entirety.

TECHNICAL FIELD

The present disclosure relates to a situation awareness system and method for vehicles.

BACKGROUND

Vehicles, such as cars, typically include displays or indicators to provide information to the vehicle operator. Such displays or indicators may, for example, provide information regarding mileage, fuel consumption, and vehicle speed.

SUMMARY

It is useful to provide situation awareness information to the vehicle operator via an ambient display coupled to the windshield in order to allow the vehicle operator to visually process the situation awareness information. To this end, the present disclosure describes a situation awareness system and method for conveying messages and information to the vehicle operator.

In an embodiment, the situation awareness method can be used to provide information to a vehicle operator via first, second, and third substantially transparent ambient displays that are coupled to a windshield of a vehicle. The situation awareness method includes the following steps: (a) monitoring a physiological state of the vehicle operator; (b) monitoring a vehicle operating parameter of the vehicle; (c) monitoring vehicle context data; (d) identifying a predetermined physiological condition based on the monitored physiological state of the vehicle operator; (e) identifying a predetermined vehicle operating condition based on the monitored vehicle operating parameter; (f) identifying a predetermined vehicle context condition based on the monitored vehicle context data; (g) adjusting a luminance of the first substantially transparent ambient display based on the identified predetermined physiological condition; (h) adjusting a luminance of the second substantially transparent ambient display based on the identified predetermined vehicle operating condition; and (i) adjusting a luminance of the third substantially transparent ambient display based on the identified predetermined vehicle context condition. The steps are not necessarily listed in chronological order.

In another embodiment, the situation awareness method includes the following steps: (a) monitoring a physiological state of the vehicle operator; (b) identifying a predetermined physiological condition based on the physiological state of the vehicle operator; and (c) adjusting a chromaticity and a luminance of the substantially transparent ambient display based on the identified predetermined physiological condition.

The present disclosure also relates to a situation awareness system of a vehicle. In an embodiment, the situation awareness system includes a windshield, at least one physiological state sensor configured to monitor a physiological state of the vehicle operator, at least one vehicle performance sensor configured to monitor at least a vehicle operating parameter, at least one vehicle context sensor configured to obtain a vehicle context data. The situation awareness system further includes first, second, and third substantially transparent ambient displays coupled to the windshield and a control module in communication with the physiological state sensor, the vehicle performance sensor, the vehicle context sensor, the first substantially transparent ambient display, the second substantially transparent ambient display, and the third substantially transparent ambient display. The control module is programmed to execute the following instructions: (a) identify a predetermined physiological condition based on the physiological state of the vehicle operator; (b) identify a predetermined vehicle operating condition based on the vehicle operating parameter; (c) identify a predetermined vehicle context condition based on the vehicle context data; and (d) command the first, second, and third substantially transparent ambient displays to adjust their chromaticity and luminance based on the identified predetermined physiological state, the identified predetermined vehicle operating condition, and the identified predetermined vehicle context condition, respectively.

The above features and advantages and other features and advantages of the present invention are readily apparent from the following detailed description of the best modes for carrying out the invention when taken in connection with the accompanying drawings.

DETAILED DESCRIPTION

Figure 1:
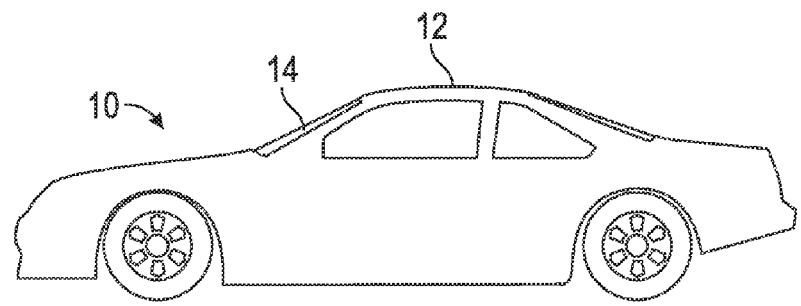
FIG. 1 is a schematic, side view of a vehicle.

Referring to the drawings, wherein like reference numbers refer to like components throughout the several figures, FIG. 1 schematically illustrates a vehicle 10 including a vehicle body 12 and a windshield 14 coupled to the vehicle body 12. The windshield 14 is also wholly or partly made of at least one substantially transparent material (e.g., glass) and the vehicle operator can therefore see through the windshield 14. A rearview mirror 105 is coupled to the windshield 14.

Figure 2:
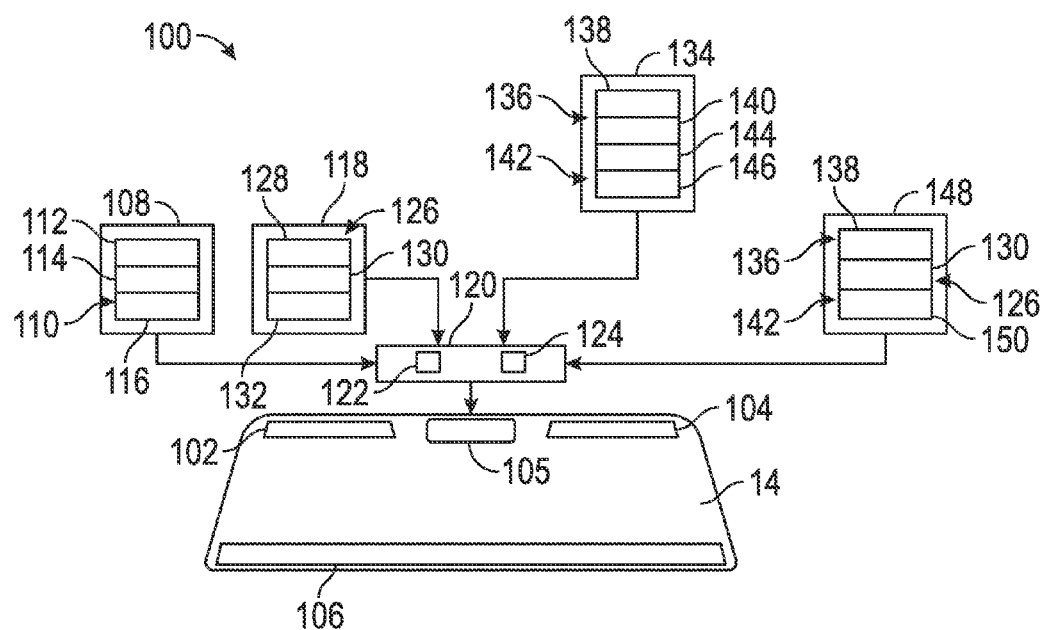
FIG. 2 is a schematic block diagram of a situation awareness system of the vehicle shown in FIG. 1.

FIG. 2 schematically depicts the windshield 14 and a situation awareness system 100 operatively coupled to the windshield 14. The vehicle 10 may be a land vehicle, such as a car, or any other type of vehicle, such as a boat, farm equipment, construction equipment, or an airplane. Irrespective of the kind of vehicle, the situation awareness system 100 can communicate information to a vehicle operator about the vehicle operating parameters, vehicle operator's physiological state, and vehicle context data. As used herein, the term "vehicle operating parameters" refers to parameters relating to the performance of the vehicle 10, such as acceleration, deceleration, vehicle speed, engine speed, wheel slip, vehicle location with respect to a lane, braking, distance to another vehicle and other parameters representative of the operation of the vehicle 10. In the present disclosure, the term "vehicle operator's physiological state" refers to the physiological information or conditions of the vehicle operator such as eye location or orientation, eye glance behavior, eye fixation, head orientation or position, inattention, heart rate, heart rate variability, percentage of eye closure (PERCLOSE) parameter, stress, sweat, respiration, and/or drowsiness. The term "vehicle context data" refers to information or parameters relating to objects or conditions around the vehicle 10, such as traffic, weather, bicycles, motorcycles, the location of pedestrians with respect to the vehicle 10, and the location of other vehicles with respect to the vehicle 10, and current route of the vehicle 10 with respect of the route of another vehicle.

With reference to FIG. 2, the situation awareness system 100 is part of the vehicle 10 and includes a first or driver ambient display 102, a second or vehicle ambient display 104, and a third or context ambient display 106. Each of the first, second, and third ambient displays 102, 104, 106 is coupled to the windshield 14. For instance, each of the first, second, and third ambient displays 102, 104, 106 may be entirely or partly embedded inside the windshield 14 or laminated to an outer surface of the windshield 14. Regardless of how they are coupled to the windshield 14, the first, second, and third ambient displays 102, 104, 106 are substantially transparent and can change their chromaticity and luminance in order to alert the vehicle operator of an identified physiological condition, an identified vehicle operating parameter, and an identified vehicle context data, respectively. For instance, each of the first, second, and third ambient displays 102, 104, 106 includes a light source, such as light-emitting diodes, (LEDs) electrically connected to an electrical power source and color-emitting particles, such as phosphor particles, capable of changing colors depending on the excitation wavelength of the light emitted by the light source. Because the first, second, and third ambient displays 102, 104, 106 are wholly or partly made of substantially transparent material, the vehicle operator can see through the first, second, and third ambient displays 102, 104, 106. For example, the visible light transmission through the first, second, and third ambient displays 102, 104, 106 may be greater than ninety (90) percent. Accordingly, the first, second, and third ambient displays 102, 104, 106 may be referred to as the first, second, and third substantially transparent ambient displays, respectively. The ambient displays 102, 104, and 106 are positioned within the parafoveal and/or peripheral portion of the driver's field of vision to enable processing of information without directly gazing upon the displays.

The situation awareness system 100 includes a control module 120 in communication (e.g., electronic communication) with the first, second, and third ambient displays 102, 104, 106. The terms "control module," "module," "control," "controller," "control unit," "processor" and similar terms mean any one or various combinations of one or more of Application Specific Integrated Circuit(s) (ASIC), electronic circuit(s), central processing unit(s) (preferably microprocessor(s)) and associated memory and storage (read only, programmable read only, random access, hard drive, etc.) executing one or more software or firmware programs or routines, combinational logic circuit(s), sequential logic circuit(s), input/output circuit(s) and devices, appropriate signal conditioning and buffer circuitry, and other components to provide the described functionality. "Software," "firmware," "programs," "instructions," "routines," "code," "algorithms" and similar terms mean any controller executable instruction sets. In the illustrated embodiment, the control module 120 includes at least one memory 122 (or any other non-transitory computer readable storage medium) and a processor 124 configured to execute computer readable instructions or steps stored in the memory 122 or any other computer readable storage medium.

In addition to the control module 120, the situation awareness system 100 includes a vehicle operator monitoring system 108 capable of monitoring the vehicle operator's physiological state. To do so, the vehicle operator monitoring system 108 includes at least one physiological sensor 110 coupled to the vehicle body 12. In the present disclosure, the term "physiological sensor" refers to a sensor capable of monitoring and measuring a physiological condition of the vehicle operator. As a non-limiting example, the vehicle operator monitoring system 108 includes an eye tracking sensor 112. The eye tracking sensor 112 can measure and monitor the vehicle operator's eye location or orientation, eye glance behavior, eye fixation, head orientation or position, and percentage of eye closure (PERCLOSE). The eye tracking sensor 112 may include a camera, and the control module 120 stores associated software to measure and monitor the vehicle's operator eye behavior. For instance, the control module 120 can determine the vehicle operator's drowsiness based on the eye and head movement, which is monitored with the eye tracking sensor 112. The physiological system(s) and/or physiological sensor(s) 110 selected for monitoring may be tailored to comply with local regulations or with user preferences.

Aside from the eye tracking sensor 112, the vehicle operator monitoring system 108 includes a galvanic skin response (GSR) sensor 114 for measuring the electrical conductance of the skin, which varies based on the moisture of the skin caused by sweat. The GSR sensor 114 can therefore measure and monitor the vehicle operator's sweat. The control module 120 stores software for determining the vehicle operator's stress levels as a function of sweat, which can be measured based on the input from the GSR sensor 114.

The vehicle operator monitoring system 108 additionally includes an electrocardiograph (ECG) sensor 116 for measuring the electrical activity of the vehicle operator's heart over a period of time. The ECG sensor 116 includes electrodes capable of being attached to the vehicle operator's skin. The control module 120 stores software for determining the vehicle operator's heart rate and the heart rate variable based on the input from the ECG sensor 116. It is contemplated that the vehicle operator monitoring system 108 may include other physiological sensors 110 aside from the ECG sensor 116, the eye tracking sensor 112, and the GSR sensor 114.

The situation awareness system 100 further includes a vehicle performance monitoring system 118 for monitoring the operating conditions of the vehicle 10 (i.e., the vehicle operating parameters or parameters). The vehicle performance monitoring system 118 includes at least one vehicle performance sensor 126 coupled to the vehicle body 12. As used herein, the term "vehicle performance sensor" means a sensor capable of monitoring and measuring at least one vehicle operating parameter, such as acceleration and speed. As a non-limiting example, the vehicle performance monitoring system 118 includes a lane tracking camera 128 for monitoring the location of the vehicle 10 with respect to a lane. The control module 120 includes software capable of determining the location of the vehicle 10 with respect to the lane based on the input from the lane tracking camera 128 in order to determine if the vehicle 10 is traveling in the lane or outside the lane. For instance, the control module 120 can identify when the vehicle 10 is departing from a lane (i.e., lane departure) based on the input from the lane tracking camera 128.

The vehicle performance monitoring system 118 also includes a radar 130 coupled to the vehicle body 12 and capable of monitoring the location and distance of the vehicle 10 with respect to other objects. As a non-limiting example, the radar 130 can monitor and measure the distance between the vehicle 10 and another vehicle while the vehicle 10 is moving. The control module 120 includes software capable of determining and estimating the distance between the vehicle 10 and another object, such as another vehicle, based on the input from the radar 130. For example, the control module 120 can determine irregular gap control between the vehicle 10 and another vehicle in front of the vehicle 10.

In addition to the radar 130, the vehicle performance monitoring system 118 includes an accelerometer 132 coupled to the vehicle body 12 and capable of monitoring and measuring the acceleration of the vehicle 10. As non-limiting examples, the vehicle performance monitoring system 118 can monitor and measure acceleration, deceleration, and braking of the vehicle 10. The control module 120 stores software capable of determining acceleration, deceleration, and braking based on the input from the accelerometer 132. For example, the control module 120 can determine uneven acceleration or deceleration based on the input from the accelerometer 132.

The situation awareness system 100 additionally includes a context monitoring system 134 for monitoring the context conditions around the vehicle 10. The context monitoring system 134 is in communication (e.g., electronic communication) with the control module 120 and includes vehicle context sensors 136 capable of monitoring and measuring vehicle context data. In the present disclosure, the term "vehicle context sensor" refers to sensors capable of monitoring and measuring vehicle context data relating to objects or conditions around the vehicle 10, such as traffic, weather, the location of pedestrians with respect to the vehicle 10, and the location of other vehicles with respect to the vehicle 10, and current route of the vehicle 10 with respect of the route of another vehicle. In the depicted embodiment, the vehicle context sensors 136 include a forward scene camera 138 for capturing an image of an object in front of the vehicle 10. The control module 120 includes software for recognizing objects, such as a car, in front of the vehicle 10 based on the input from the forward scene camera 138.

Additionally or alternatively, the vehicle context sensors 136 include a panoramic camera 140 capable of capturing images three hundred sixty (360) degrees around the vehicle 10. The control module 120 includes software for recognizing objects, such as cars and pedestrians, located around the vehicle 10 based on the input from the panoramic camera 140.

The context monitoring system 134 can also receive external inputs 142 from external systems. For example, in the depicted embodiment, the context monitoring system 134 can receive a weather input 144 concerning the weather around the surrounding area of the vehicle 10. The control module 120 can determine weather conditions, such as icy roads, based on the weather input 144.

Another external input 142 may be a traffic input 146. Thus, the context monitoring system 134 can receive traffic input 146 concerning traffic conditions along the current route of the vehicle 10. The control module 120 can then determine the traffic conditions along the current or projected route of the vehicle 10 based on the traffic input 146.

The situation awareness system 100 further includes a vehicle occurrence assessment system 148 for monitoring occurrences around the vehicle 10. The vehicle occurrence assessment system 148 is in communication (e.g., electronic communication) with the control module 120 and includes vehicle context sensors 136 capable of monitoring and measuring vehicle context data and vehicle operating parameter, respectively. In the depicted embodiment, the vehicle occurrence assessment system 148 includes a forward scene camera 138, which may be the forward scene camera 138 of the context monitoring system 134. The forward scene camera 138 can capture images of objects in front of the vehicle 10. The control module 120 includes software capable of detecting objects, such as other vehicles or pedestrians, in front of the vehicle 10 based on the input from the forward scene camera 138.

In addition to the forward scene camera 138, the vehicle occurrence assessment system 148 may include a radar 130, which may be the same radar 130 of the vehicle performance monitoring system 118. The radar 130 can monitor and detect the location, speed, and movement direction of other objects, such as vehicles, with respect to the vehicle 10. The control module 120 includes software capable of determining if it is likely that the trajectory of vehicle 10 will be in conflict with that of another object based on the input from the radar 130.

The vehicle occurrence assessment system 148 may also receive external inputs 142 from external systems in order to determine the likelihood that a particular event will occur. For instance, the vehicle occurrence assessment system 148 includes an external input 142 from an automatic dependent surveillance-broadcast (ADS-B) 150 system. The ADS-B system 150 may communicate data to the control module 120 relating to the movement and location of other objects, such as emergency vehicles. The control module 120 includes software capable of determining a conflict, probe, and resolution route to prevent the vehicle 10 from encountering the other object (e.g., emergency vehicle).

The control module 120 is configured to control the luminance and chromaticity of the first, second, and third ambient displays 102, 104, 106 based, at least in part, on the input received from the physiological sensors 110, the vehicle performance sensors 126, the vehicle context sensors 136, and external inputs 142. To do so, the control module 120 is specifically programmed to execute (via the processor 124) the steps of a situation awareness method 200 (FIG. 3).

Figure 3:
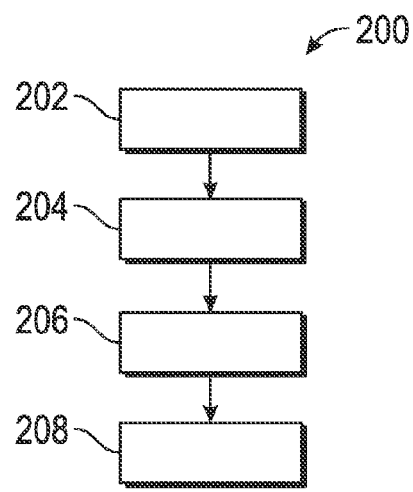
FIG. 3 is a flowchart of a method for controlling the situation awareness system of FIG. 2.

With reference to FIG. 3, the situation awareness method 200 begins at step 202, which entails monitoring the physiological state of the vehicle operator, the vehicle operating parameters, and the vehicle context data. As discussed above, the physiological sensor 110 can monitor the physiological state of the vehicle operator; the vehicle performance sensor 126 can monitor the vehicle operating parameters; and the vehicle context sensors 136 and external inputs 142 can monitor the vehicle context data. Then, the situation awareness method 200 continues to step 204. As non-limiting examples, step 202 includes monitoring a gaze location and movement and PERCLOSE parameter of the vehicle operator using the eye tracking sensor 112, monitoring the heart rate and heart rate variability of the vehicle operator using the ECG sensor 116, and monitoring a galvanic skin response of the vehicle operator using the GSR sensor 114. Further, step 202 may also include monitoring a location of the vehicle 10 with respect to the lane in which the vehicle 10 is travelling using the lane tracking camera 128, monitoring vehicle acceleration using the accelerometer 132, and monitoring the location of the vehicle with respect to another object, such as another vehicle, using the radar 130. Moreover, step 202 may include monitoring the current route traveled by the vehicle 10 based on an external input 142, monitoring the recorded occurrences along the current route based on the input from the ADS-B system 150.

In step 204, the control module 120 receives data regarding the physiological state of the vehicle operator, the vehicle operating parameters, and the vehicle context data from the physiological sensors 110, the vehicle performance sensors 126, the vehicle context sensors 136, and the external inputs 142. In other words, step 204 entails receiving, via the control module 120, data relating to the physiological state of the vehicle operator, the vehicle operating parameters, and the vehicle context data. Therefore, the control module 120 is specifically programmed to receive data relating to the physiological state of the vehicle operator, the vehicle operating parameters, and the vehicle context data. Once the control module 120 receives such data, the situation awareness method 200 proceeds to step 206.

Step 206 entails identifying, via the control module 120, one or more predetermined physiological conditions of the vehicle operator based on the monitored physiological state of the vehicle operator, one or more predetermined vehicle operating conditions based on the monitored vehicle operating parameters, and one or more vehicle context conditions based on the monitored vehicle context data. Accordingly, the control module 120 is specifically programmed to identify the one or more predetermined physiological conditions of the vehicle operator based on the monitored physiological state of the vehicle operator, one or more predetermined vehicle operating conditions based on the monitored vehicle operating parameters, and one or more vehicle context conditions based on the monitored vehicle context data.

In the present disclosure, the term "predetermined physiological condition" refers to one or more vehicle operator's physiological state as measured by the physiological sensors 110 that is greater or less than a predetermined threshold value or that falls within or outside a predetermined range. For example, the predetermined physiological condition may be a condition in which the time that the vehicle operator's eyes are fixed in a position other than the windshield 14 as determined by the eye tracking sensor 112 is greater than an upper time threshold value (e.g., 20 seconds). In another example, the predetermined physiological condition may be a condition in which the vehicle operator's PERCLOSE value as determined by the eye tracking sensor 112 is lower than a lower PERCLOSE threshold value. Further, the predetermined physiological condition may be a condition in which a vehicle operator's skin conductance as measured by the GSR sensor 114 is greater than an upper skin conductance threshold value. Moreover, the predetermined physiological condition may be a condition in which the vehicle operator's heart rate as measured by the ECG sensor 116 is greater than an upper heart rate threshold value or less than a lower heart rate threshold value. Similarly, the predetermined physiological condition may be a condition in which the vehicle operator's heart rate variability as measured by the ECG sensor 116 is greater than an upper heart rate variability threshold value or less than a lower heart rate variability threshold value. As a non-limiting example, the predetermined physiological state conditions may be under or over arousal physiological state conditions in accordance with the Yerkes-Dodson law. Accordingly, the control module 120 can determine that the vehicle operator is too passive, which is one of the predetermined physiological conditions based on the fact that the limited gaze shifting, heart rate, heart rate variability, and the PERCLOSE parameter are all below a predetermined threshold. Conversely, the control module 120 can determine the vehicle operator is too excited, which is one of the predetermined physiological conditions, based on the fact that the vehicle operator's eyes are fixed to a specific location, the GSR conductance is higher than a predetermined threshold, and that heart rate and heart rate variability are above predetermined thresholds.

In step 206, the control module 120 can also identify one or more predetermined vehicle operating conditions based on monitored vehicle operating parameters. As non-limiting examples, the predetermined vehicle operating conditions may include lane departures, irregular gap control between the vehicle 10 and another vehicle, acceleration above or below a predetermined threshold, deceleration above or below a predetermined threshold, and braking rate above or below a predetermined threshold. In the present disclosure, the term "predetermined vehicle operating condition" refers to a vehicle condition as measured by the vehicle performance sensors 126 that is greater or less than a predetermined threshold value or that falls within or outside a predetermined range. For example, the predetermined vehicle operating condition may be a condition in which the vehicle is driving completely or partially outside a lane for a time (as determined by the lane tracking camera 128) that is greater than an upper time threshold value. Further, the predetermined vehicle operating condition may be a condition in which the distance from the vehicle 10 to another vehicle (as determined by the radar 130) is less than a lower distance threshold value. Moreover, the predetermined vehicle operating condition may be a condition in which acceleration, deceleration, and braking of the vehicle 10 (as measured by the accelerometer 132) are greater than or less than a predetermined threshold value.

In the present disclosure, the term "predetermined vehicle context condition" includes vehicle context conditions or parameters as measured by the vehicle context sensors 136 or determined by the external inputs 142 that are greater or less than a predetermined threshold value or that fall within or outside a predetermined range. For instance, the predetermined vehicle context condition may be a condition in which the distance from the vehicle 10 and another object in front of the vehicle 10, such as a car or pedestrian, (as determined by the forward scene camera 138) is less than a predetermined distance threshold value. Further, the predetermined vehicle context condition may be a condition in which the distance from the vehicle 10 to another object (e.g., vehicle or pedestrian) around the vehicle 10 (as determined by the panoramic camera 140) is less than a predetermined distance threshold value. Moreover, the predetermined vehicle context condition may be a condition in which a specific kind of weather related event (e.g., icy roads, rain, windy) is identified by the weather input 144. Furthermore, the predetermined vehicle context condition may be a condition in which the speed of traffic along a predetermined route (as determined by the traffic input 146) is less than a predetermined speed threshold value. Also, the predetermined vehicle context condition may be a condition in which a potential conflict is detected based on the input from the ADS-B system 150 in which the vehicle 10, which is traveling along a first route, will be in conflict with another vehicle (e.g., emergency vehicle) traveling along a second route. After identifying the predetermined vehicle operation condition, the predetermined physiological conditions, the predetermined vehicle context condition or any combination thereof, the situation awareness method 200 proceeds to step 208.

Step 208 entails adjusting the chromaticity and luminance of the first, second, and third ambient displays 102, 104, 106 based on the identified predetermined physiological condition, the identified predetermined vehicle operating condition, and the identified predetermined vehicle context condition, respectively. To do so, the control module 120 is specifically programmed to command the first, second, and third ambient displays 102, 104, 106 to adjust their chromaticity and luminance based on the identified predetermined physiological condition, the identified predetermined vehicle operating condition, and the identified predetermined vehicle context condition, respectively. For example, upon receipt of a command, the control module 120 can adjust the luminance of the first, second, and third ambient displays 102, 104, 106 by increasing or decreasing the luminance at a constant or by modulating the luminance at a predetermined constant or variable frequency based on the identified predetermined physiological condition, the identified predetermined vehicle context condition, or the identified vehicle operating condition. The modulation of the luminance may be a sinusoidal luminance variation at a predetermined frequency and can be achieved by adjusting the duty cycle of the electrical current received by the light sources of the first, second, and third ambient displays 102, 104, 106. The overall luminance adjustment can be achieved by adjusting the magnitude of the electrical current received by the light sources of the first, second, and third ambient displays 102, 104, 106.

As discussed above, step 208 also entails adjusting the chromaticity of the first, second, and third ambient displays 102, 104, 106 based on the identified predetermined physiological condition, the identified predetermined vehicle operating condition, and the identified predetermined vehicle context condition, respectively. For instance, upon receipt of a command from the control module 120, the first ambient display 102 can emit an amber light based on the identified predetermined physiological condition. The second ambient display 104 can emit a red light based on the identified predetermined vehicle operating condition. The chromaticity adjustment can be achieved by adjusting the wavelength of the light emitted by the light source (and receives by color-emitting particles) of the first, second, and third ambient displays 102, 104, 106.

Figure 4:
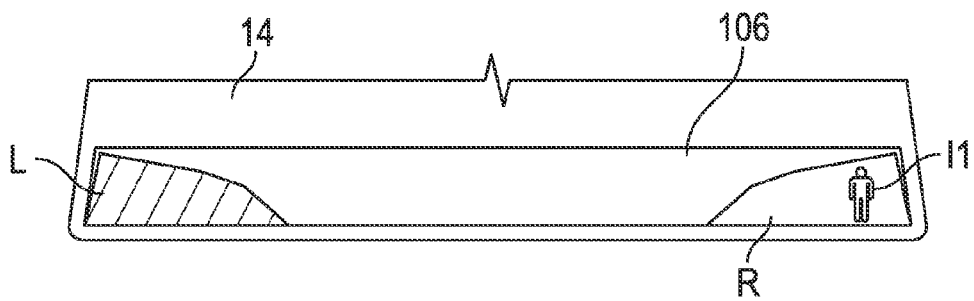
FIG. 4 is a schematic, front view of part of the windshield of the vehicle of FIG. 1, wherein the context ambient display showing icons on one side and a visible color glow on the other side.
Figure 5:
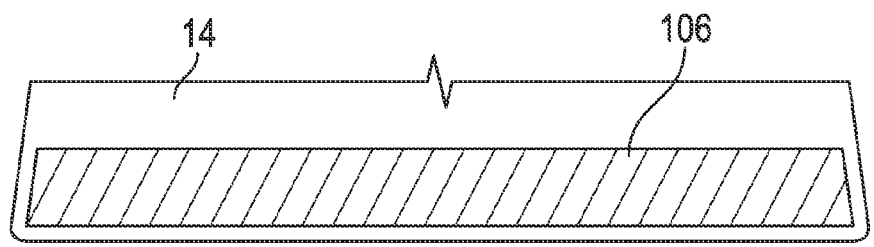
FIG. 5 is a schematic, front view of part of the windshield of the vehicle of FIG. 1, wherein the entire context ambient display is glowing.

The third ambient display 106 (or any other ambient display) can emit a visible light, such as a red light, along only part of the third ambient display 106 (as shown in FIG. 4) or along the entire third ambient display 106 (as shown in FIG. 5) based on the predetermined vehicle context condition. As a non-limiting example, the third ambient display 106 (or any other ambient display) can emit a red light only on the left section L of the ambient display 106 to indicate, for instance, that an object (e.g., another vehicle) is on the left side of the vehicle 10. The entire third ambient display 106 can emit a red flashing light to alert the vehicle operator of an imminent occurrence relating to another object.

Figure 6:
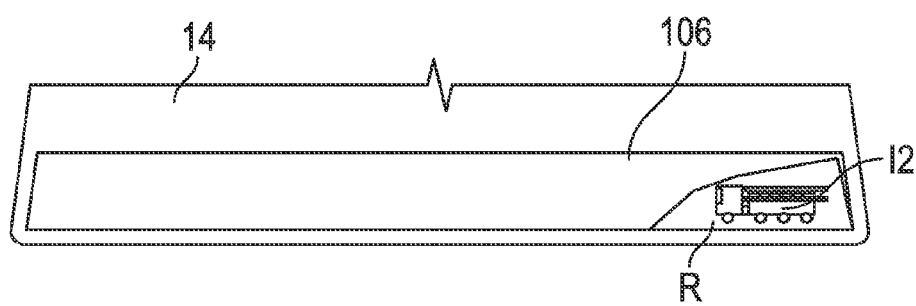
FIG. 6 is a schematic, front view of part of the windshield of the vehicle of FIG. 1, wherein the context ambient display is projecting an icon only on its right side.

The third ambient display 106 can emit a red light so as to form an icon I1 on a right section R of the third ambient display 106 to alert the vehicle operator that something (e.g., a pedestrian) is on the right side of the vehicle 10. Thus, step 208 may include displaying the icon I1 via the third ambient display 106 (or any other ambient display) based on the identified predetermined vehicle context condition, identified predetermined vehicle operating condition, identified physiological condition, or any combination thereof. In the present disclosure the icon I1 resembles a pedestrian in order to alert the vehicle operator that a pedestrian is on the right side of the vehicle 10. However, the third ambient display 106 (or any other ambient display) may display other icons, such as icon I2 shown in FIG. 6. The icon I2 resembles an emergency vehicle and can alert the vehicle operator that an emergency vehicle is on the right side of the vehicle 10.

In addition to the icon I1, the third ambient display 106 (or any other ambient display) may present information using affective computing. In the present disclosure, the term "affective computing" refers to computing systems that simulate human emotions. For example, the third ambient display 106 (or any other ambient display) may present human-like images with various hand and facial expressions that convey particular emotions. Further, the third ambient display 106 (or any other ambient display) may present emotion gages or images conveying a particular predetermined vehicle operating condition or predetermined vehicle context condition. Further, the control module 120 can compare and cross-reference the current route traveled by the vehicle 10 with certain recorded occurrences, such as the current route of an emergency vehicle, along to the current route and, in response, the third ambient display 106 presents the icon I2, which resembles the emergency vehicle.

While the best modes for carrying out the invention have been described in detail, those familiar with the art to which this invention relates will recognize various alternative designs and embodiments for practicing the invention within the scope of the appended claims.

The invention claimed is:

1. A situation awareness method of providing information to a vehicle operator, the method comprising:
   monitoring a physiological state of the vehicle operator;
   monitoring a vehicle operating parameter of the vehicle;
   monitoring a vehicle context data;
   identifying a predetermined physiological condition based on the monitored physiological state of the vehicle operator;
   identifying a predetermined vehicle operating condition based on the monitored vehicle operating parameter;
   identifying a predetermined vehicle context condition based on the monitored vehicle context data;
   adjusting a luminance of a first substantially transparent ambient display based on the identified predetermined physiological condition;
   adjusting a luminance of a second substantially transparent ambient display based on the identified predetermined vehicle operating condition; and
   adjusting a luminance of a third substantially transparent ambient display based on the identified predetermined vehicle context condition.

2. The situation awareness method of claim 1, wherein adjusting the luminance of the first, second, and third substantially transparent ambient displays includes modulating the luminance of the first, second, and third substantially transparent ambient displays at a predetermined frequency based on the identified predetermined physiological condition, the identified predetermined driving condition, and the identified predetermined vehicle context condition, respectively.

3. The situation awareness method of claim 1, further comprising adjusting a chromaticity of the first, second, and third substantially transparent ambient displays based on the identified predetermined physiological condition, the identified predetermined driving condition, and the identified predetermined vehicle context condition, respectively.

4. The situation awareness method of claim 3, further comprising emitting an amber light via the first substantially transparent ambient display based on the identified predetermined physiological condition.

5. The situation awareness method of claim 3, further comprising emitting a red light via the second substantially transparent ambient display based on the identified predetermined vehicle operating condition.

6. The situation awareness method of claim 3, further comprising emitting a red light via the third substantially transparent ambient display along only part of the third substantially transparent ambient display based on the identified predetermined vehicle context condition.

7. The situation awareness method of claim 1, further comprising displaying an icon on the third substantially transparent ambient display based on the identified predetermined vehicle context condition.

8. The situation awareness method of claim 1, wherein monitoring the physiological state of the vehicle operator includes monitoring a gaze location of the vehicle operator.

9. The method of claim 1, wherein monitoring the physiological state of the vehicle operator includes monitoring a heart rate of the vehicle operator.

10. The situation awareness method of claim 1, wherein monitoring the physiological state of the vehicle operator includes monitoring a heart rate variability of the vehicle operator.

11. The situation awareness method of claim 1, wherein monitoring the physiological state of the vehicle operator includes monitoring a galvanic skin response of the vehicle operator.

12. The situation awareness method of claim 1, wherein the monitoring vehicle operating parameter includes monitoring a location of the vehicle with respect to a lane in which the vehicle is traveling.

13. The situation awareness method of claim 1, wherein monitoring the vehicle operating parameter includes monitoring vehicle acceleration.

14. The situation awareness method of claim 1, wherein monitoring the vehicle operating parameter includes monitoring a location of the vehicle with respect to another vehicle.

15. The situation awareness method of claim 1, wherein monitoring context conditions includes monitoring a current route traveled by the vehicle; monitoring recorded occurrences along the current route; and comparing and cross-referencing the current route traveled by the vehicle with the recorded occurrences along to the current route.

16. A situation awareness system for a vehicle, comprising:
 a windshield;
 at least one physiological state sensor configured to monitor a physiological state of a vehicle operator;
 a first substantially transparent ambient display coupled to the windshield;
 at least one vehicle performance sensor configured to monitor at least a vehicle operating parameter;
 a second substantially transparent ambient display coupled to the windshield;
 at least one vehicle context sensor configured to monitor vehicle context data;
 a third substantially transparent ambient display coupled to the windshield;
 a control module in communication with the at least one physiological state sensor, the at least one vehicle performance sensor, the at least one vehicle context sensor, the first substantially transparent ambient display, the second substantially transparent ambient display, and the third substantially transparent ambient display;
 wherein the control module is programmed to:
  identify a predetermined physiological condition based on the physiological state of the vehicle operator;
  identify a predetermined vehicle operating condition based on the vehicle operating parameter;
  identify a predetermined vehicle context condition based on the vehicle context data; and
  command the first, second, and third substantially transparent ambient displays to adjust a chromaticity and a luminance thereof based on the identified predetermined physiological condition, the identified predetermined driving condition, and the identified predetermined vehicle context condition, respectively.

* * * * *